United States Patent
Bosché et al.

(10) Patent No.: US 7,858,120 B2
(45) Date of Patent: Dec. 28, 2010

(54) PHARMACEUTICAL FORMULATIONS CONTAINING FLAVOURING SUBSTANCES WITH IMPROVED PHARMACEUTICAL PROPERTIES

(75) Inventors: Patrick Bosché, Grenzach-Whylen (DE); Sabine Bongaerts, Leverkusen (DE); Venkata-Rangarao Kanikanti, Leverkusen (DE)

(73) Assignee: Bayer Animal Health GmbH (DE)

( * ) Notice: Subject to any disclaimer, the term of this patent is extended or adjusted under 35 U.S.C. 154(b) by 604 days.

(21) Appl. No.: 10/576,408

(22) PCT Filed: Oct. 30, 2004

(86) PCT No.: PCT/EP2004/012327

§ 371 (c)(1),
(2), (4) Date: Jan. 5, 2007

(87) PCT Pub. No.: WO2005/044271

PCT Pub. Date: May 19, 2005

(65) Prior Publication Data

US 2007/0196466 A1      Aug. 23, 2007

(30) Foreign Application Priority Data

Nov. 4, 2003   (DE)   ................. 103 51 448

(51) Int. Cl.
*A61K 9/20*       (2006.01)
*A61K 31/496*    (2006.01)
(52) U.S. Cl. ................... 424/464; 424/465; 514/253.08
(58) Field of Classification Search ................ 424/464, 424/465, 442; 514/253.08
See application file for complete search history.

(56) References Cited

U.S. PATENT DOCUMENTS

| | | | |
|---|---|---|---|
| 5,152,986 A * | 10/1992 | Lange et al. ............. 424/78.14 |
| 5,256,699 A | 10/1993 | Murphy et al. | |
| 5,328,908 A * | 7/1994 | Demuth et al. ......... 514/253.08 |
| 5,681,577 A | 10/1997 | Lech et al. | |
| 5,776,240 A | 7/1998 | Deller et al. | |
| 5,808,076 A | 9/1998 | Vetter et al. | |
| 6,596,311 B1 | 7/2003 | Dobetti | |
| 2001/0018417 A1 | 8/2001 | Carson et al. | |
| 2003/0170310 A1* | 9/2003 | Wadhwa ..................... 424/486 |
| 2003/0229101 A1 | 12/2003 | Sherman | |
| 2004/0043925 A1 | 3/2004 | Kalbe et al. | |
| 2004/0254210 A1 | 12/2004 | Haeberlin et al. | |

FOREIGN PATENT DOCUMENTS

| | | |
|---|---|---|
| CA | 3413698 A1 * | 12/2002 |
| DE | 102 50 711 A1 | 5/2004 |
| EP | 0345787 B1 | 11/1992 |
| EP | 0693281 A2 | 1/1996 |
| EP | 1177788 A2 * | 2/2002 |
| WO | 9805305 | 2/1998 |
| WO | WO 01/12162 | 2/2001 |
| WO | 01/64183 A1 | 9/2001 |
| WO | WO 2004/039349 | 5/2004 |

OTHER PUBLICATIONS

Daube, G. et al. Orally Administered Pharmaceutical preparation active agent bonded to ion exchanger, DE 10224086, Derwent Abstract, pp. 1-4.*
Pradofloxacin, The Merck Index, 2006, 2009 14th Edition, version 14.4.*
Enrofloxacin, The Merck Index, 2006, 2009, 14th Edition, version 14.4.*

* cited by examiner

*Primary Examiner*—Johann Richter
*Assistant Examiner*—Andriae M Holt (57) ABSTRACT

The invention relates to flavoring-containing pharmaceutical formulations with improved pharmaceutical properties, and to process for the production thereof.

2 Claims, 10 Drawing Sheets

PHARMACEUTICAL FORMULATIONS CONTAINING FLAVOURING SUBSTANCES WITH IMPROVED PHARMACEUTICAL PROPERTIES

The invention relates to flavouring-containing pharmaceutical formulations with improved pharmaceutical properties, and to process for the production thereof.

The use of flavourings in pharmaceutical formulations is becoming increasingly important in the veterinary medical sector. The flavourings are intended to facilitate administration of solid drug forms to animals, especially dogs or cats. Flavourings available on the market, such as, for example, Trigarol Bayopal P® (Haarmann und Reimer GmbH, Holzminden, D) or Artificial Beef Flavor (Pharma Chemie, Syracuse, Nebr., USA) have an adverse effect on the pharmaceutical properties of tablets. Thus, for example, the tablet hardness (determination of tablet hardness described for example in Bauer, Kurt H.; Frömming, Karl-Heinz; Führer, Claus: Lehrbuch der Pharmazeutischen Technologie, 6th revised and corrected edition 1999) is reduced or the stability of the tablets is adversely affected by a deterioration in release or tablet hardness. These changes result in disadvantages for the quality of the pharmaceutical products.

Botzolakis, Harris and Nesbitt describe in Pharm. Res. (5, No. 10, Suppl. S253, 1988) and in EP-A 0345787 or U.S. Pat. No. 4,910,023 formulations with unpleasantly tasting active ingredients and processes for their production. In this case, unpleasantly tasting, hygroscopic active ingredients are suspended in water and dried in combination with colloidal silicon dioxide. This results in pleasantly tasting, less hygroscopic tablets.

The requirements to be met by a solid pharmaceutical formulation suitable for administration to animals are diverse:
- good acceptance by the animals, in the best case voluntary intake
- good storage stability, especially low tendency to absorb water
- good mechanical properties, especially tablet hardness
- good disintegration and release properties.

The increased acceptance can be achieved by adding flavourings. The problem existing in this connection to date is that these flavourings cause a deterioration in the pharmaceutical properties of the corresponding solid formulations.

It has now been found, surprisingly, that the disadvantageous effects of flavouring can be reduced or completely compensated by adding comparatively large amounts of colloidal silicon dioxide, and the resulting solid pharmaceutical formulations display good or very good properties in all the abovementioned criteria. It is noteworthy in this connection that the colloidal silicon dioxide scarcely influences the effect of the flavourings although it is proposed in the state of the art for taste masking.

The invention therefore relates to solid pharmaceutical formulations comprising an active pharmaceutical ingredient, a flavouring and at least 1.5% by weight of colloidal silicon dioxide based on the total weight of the finished formulation.

The pharmaceutical formulations of the invention normally comprise the active pharmaceutical ingredient in an amount of 0.001-90% by weight.

Suitable active pharmaceutical ingredients are in general all those customary in veterinary medicine. Examples which may be mentioned are: quinolone antibiotics, and agents for treating cancers, especially MMP inhibitors.

Quinolone antibiotics are described inter alia in the following documents: U.S. Pat. No. 4,670,444 (Bayer AG), U.S. Pat. No. 4,472,405 (Riker Labs), U.S. Pat. No. 4,730,000 (Abbott), U.S. Pat. No. 4,861,779 (Pfizer), U.S. Pat. No. 4,382,892 (Daiichi), U.S. Pat. No. 4,704,459 (Toyama), as specific examples of quinolone antibiotics which may be mentioned are: ciprofloxacin, enrofloxacin, ibafloxacin, sarafloxacin, difloxacin, binfloxacin, danofloxacin, marbofloxacin, benofloxacin, ofloxacin, orbifloxacin, tosufloxacin, temafloxacin, pipemidic acid, norfloxacin, pefloxacin, levofloxacin, fleroxacin. Further suitable quinolone antibiotics which may be mentioned are the compounds described in WO 97/31001, especially, pradofloxacin (8-cyano-1-cyclopropyl-7-((1S, 6S)-2,8-diaiabicyclo[4.3.0]nonan-6-fluoro-1,4-dihydro-4oxo-3-quinolinecarboxylic acid) of the formula Preferred quinolone antibiotics are described in general by the formulae (I) and (II)

in which

A is nitrogen or =C—R$^4$,

R$^4$ is hydrogen, fluorine, chlorine, cyano, nitro or methyl,

B is

-continued and $R^5$ is hydrogen, a branched or unbranched alkyl group having 1 to 4 carbon atoms, which may optionally be substituted by a hydroxyl or methoxy group, $R^6$ is hydrogen, methyl or phenyl, $R^7$ is hydrogen or methyl, $R^8$ is amino, alkyl- or dialkylamino having 1 or 2 carbon atoms in the alkyl group, aminomethyl, alkyl- or dialkylaminomethyl having 1 or 2 carbon atoms in the alkyl group, $R^1$ is an alkyl radical having 1 to 3 carbon atoms, cyclopropyl, 2-fluoroethyl, vinyl, methoxy, 4-fluorophenyl or methylamino,

$R^2$ is hydrogen, alkyl having 1 to 6 carbon atoms, and cyclohexyl, benzyl, 2-oxopropyl, phenacyl and ethoxycarbonylmethyl, $R^3$ is hydrogen, methyl or ethyl, Z is oxygen, methyl- or phenyl-substituted nitrogen, and —CH$_2$—, and their pharmaceutically usable salts.

Preferred active ingredients are quinolonecarboxylic acids and their derivatives of the formula (Ia)

in which

B is and

A, $R^2$, $R^5$, $R^6$ and $R^7$ have the meaning indicated above.

Particularly preferred active ingredients are quinolonecarboxylic acid and its derivatives of the formula (Ia)

in which $R^2$ is hydrogen, alkyl having 1 to 4 carbon atoms, and benzyl, 2-oxopropyl, phenacyl and ethoxycarbonylmethyl, B is $R^5$ is hydrogen, methyl or ethyl, $R^6$ is hydrogen or methyl, $R^7$ is hydrogen or methyl, and A has the meaning indicated above.

Particular mention may be made of the following quinolonecarboxylic acids and their derivatives as active ingredients: 1-cyclopropyl-6-fluoro-1,4-dihydro-4-oxo-7-(1-piperazinyl)quinoline-3-carboxylic acid (cipro-floxacin), 1-cyclopropyl-6-fluoro-1,4-dihydro-4-oxo-7-(4-methyl-1-piperazinyl)quinoline-3-carboxylic acid, 1-cyclopropyl-6-fluoro-1,4-dihydro-4-oxo-7-(4-ethyl-1-piperazinyl) quinoline-3-carboxylic acid (enrofloxacin), 1-ethyl-6-fluoro-1,4-dihydro-4-oxo-7-(4-methyl-1-piperazinyl)-quinoline-3-carboxylic acid, 1-ethyl-6-fluoro-1,4-dihydro-4-oxo-7-(1-piperazinyl)quinoline-3-carboxylic acid, 1-ethyl-6-fluoro-1,4-dihydro-4-oxo-7-(1-piperazinyl)-1,8-naphthyridine-3-carboxylic acid, 9-fluoro-3-methyl-10-(4-methyl-1-piperazinyl)-7-oxo-2,3-dihydro-7H-pyrido-[1,2,3-de]-1,4-benzoxazine-6-carboxylic acid and the pharmaceutically usable salts thereof, and the methyl and ethyl esters of these compounds.

Enrofloxacin and pradofloxacin, and the pharmaceutically usable salts thereof, are very particularly preferably employed.

Pharmaceutically usable salts which may be mentioned are physiologically tolerated acid addition salts, and salts with bases. The salts are known or can be prepared in analogy to known processes.

Examples of acids which may be mentioned are: hydrochloric acid, sulphuric acid, phosphoric acid, organic acids such as formic acid, acetic acid, lactic acid, malic acid, fumaric acid, citric acid, ascorbic acid, succinic acid, tartaric acid, malonic acid, maleic acid, embonic acid.

Hydrochloric acid, acetic acid, lactic acid, embonic acid may be mentioned as preferred.

Examples of salts with bases are the alkali metal, alkaline earth metal, silver and guanidinium salts of the underlying carboxylic acids. Examples of suitable bases which may be mentioned are inorganic bases such as NaOH, KOH, Ca(OH)$_2$, ammonia, organic bases such as amines such as mono-, di-, trialkylamines, substituted amines such as ethanolamine, cyclic amines such as morpholine, piperazine, basic amino acids such as arginine, lysine, choline, N-methylglucamine.

The following bases are preferred: NaOH, KOH, ethanolamine, lysine, N-methylglucamine.

The following bases are particularly preferred: NaOH, KOH.

Pharmaceutically acceptable solvates, in particular hydrates, of the active ingredients or of the salts etc. can likewise be employed.

The active ingredients are known or can be prepared in analogy to known processes.

Suitable MMP inhibitors are described in detail in WO 96/15 096, express reference being made to this document. Among the compounds disclosed therein, those having basic biphenyl structures are preferred; a particularly preferred example which may be mentioned is the compound tanomastat:

Pharmaceutically acceptable salts, hydrates etc. can likewise be employed.

The flavourings employed according to the invention constitute mixtures of proteins, fats and carbohydrates which are specifically processed. Particular mention may be made of Trigarol Bayopal P®, of Haarmann & Reimer, and Artificial Beef Flavor® of Pharma Chemie (Syracuse, Nebr., USA). The flavourings are employed in the pharmaceutical formulations of the invention in an amount of 1-40% by weight, based on the total weight of the finished formulation, preferably 2.5-30% by weight, in particular 4-20% by weight.

Colloidal silicon dioxide is described for example in the European Pharmacopoeia (Ph. Eur., SILICA, COLLODAL ANHYDROUS) or US Pharmacopeia (USP, Colloidal Silicon dioxide). Examples of commercial products are Aerosil (Degussa), Dissolvurol or Entero-Teknosal.

The solid pharmaceutical formulations of the invention comprise at least 1.5% by weight of colloidal silicon dioxide based on the total weight of the finished formulation, and they preferably contain at least 2.5% by weight, particularly preferably at least 4% by weight, of colloidal silicon dioxide based on the total weight of the finished formulation. The solid pharmaceutical formulations of the invention normally comprise not more than 15% by weight, preferably not more than 10% by weight, of colloidal silicon dioxide. Within the limits indicated above, it has proved to be particularly advantageous to process the colloidal silicon dioxide in the colloidal silicon dioxide to flavouring ratio by weight of from 1:4 to 1:1.

A process for producing the solid pharmaceutical formulations of the invention has also been found, in which the flavouring is granulated with the colloidal silicon dioxide and one or more active ingredients and pharmaceutically usual excipients. Suitable variants for the production process of the invention are as follows:

addition of the flavouring and of the colloidal silicon dioxide to the admixture (i.e. to granules consisting of the other ingredients), mixing of the solid components, where appropriate after screening, for example through a sieve with a mesh width of 0.5-2 mm, in a suitable container for 2-30 minutes aqueous granulation of the flavouring with the colloidal silicon dioxide using binder solutions consisting of water or water with, for example, starches (maize starch, rice starch, wheat starch, potato starch), modified starches (pregelatinized starch, hydroxyethyl starch), gelatin, tragacanth, cellulose derivatives (methylcellulose, hydroxypropylmethylcellulose, hydroxypropylcellulose, sodium carboxymethylcellulose) or polyvinylpyrrolidone, addition of these granules to the admixture (i.e. to granules consisting of the other ingredients) or to the further granulation alcoholic (e.g. ethanolic) granulation of the flavouring with the colloidal silicon dioxide, addition of these granules to the admixture or to the further granulation granulation of the flavouring with the colloidal silicon dioxide using a further binder, addition of these granules to the admixture or to the further granulation addition of the flavouring with the colloidal silicon dioxide to the granulation of the active ingredient, possibly with the addition of further excipients such as, for example, fillers, disintegrants or binders.

The granulation may take place by means of a high-speed mixer as wet granulation with subsequent drying for example in a fluidized bed or tray dryer with inlet air temperatures of 40-120° C., or as granulation for example in a fluidized bed granulator.

The pharmaceutical formulations of the invention are suitable for use in veterinary medicine, e.g. in livestock management and in livestock breeding. They can be administered to agricultural and breeding livestock, zoo, laboratory and experimental animals and pets.

The agricultural and breeding livestock include mammals such as, for example, cattle, horses, sheep, pigs, goats, camels, water buffalos, donkeys, rabbits, fallow deer, reindeer, fur-bearing animals such as, for example, mink, chinchilla, racoon, birds such as, for example, chickens, geese, turkeys, ducks, pigeons, and bird species for keeping at home and in zoos. Productive and ornamental fish are also included.

The laboratory and experimental animals include mice, rats, guinea pigs, golden hamsters, dogs and cats.

Pets include dogs and cats.

The solid pharmaceutical formulations of the invention are preferably tablets. However, other solid preparations are also suitable, such as powders, premixes or concentrates, granules, pellets, boli, capsules, aerosols and inhalations.

The solid pharmaceutical formulations of the invention may comprise further pharmaceutically acceptable additives and excipients such as, for example, carriers, and the excipients detailed hereinafter.

Carriers which may be mentioned are all physiologically tolerated inert solids. Inorganic and organic substances are used as such. Examples of inorganic substances are sodium chloride, carbonates such as calcium carbonate, bicarbonates, aluminium oxides, silicas, aluminas, phosphates.

Examples of organic substances are sugars, lactose, mannitol, cellulose, human and animal foods such as milk powder, animal meals, ground and crushed grains, starches.

Excipients are antioxidants such as, for example, ascorbic acid, tocopherol, colours, which are approved for use in animals and can be employed in solution or suspension.

Further suitable excipients are lubricants and glidants such as, for example, magnesium stearate, stearic acid, talc, bentonites, disintegration-promoting substances such as starch and starch derivatives, croscarmellose sodium or crosslinked polyvinylpyrrolidone, binders such as, for example, starches (maize starch, rice starch, wheat starch, potato starch), modified starches (pregelatinized starch, hydroxyethyl starch), gelatin, tragacanth, cellulose derivatives (methylcellulose, hydroxypropylmethylcellulose, hydroxypropylcellulose, sodium carboxymethylcellulose) or polyvinylpyrrolidone, and dry binders such as microcrystalline cellulose.

EXAMPLES

I. Enrofloxacin Tablets

Enrofloxacin

TABLE 1

Formulations investigated:
Tablet compositions [mg/tablet]

| Ingredient | Standard | Example 1 5% Bayopal | Example 2 10% Bayopal | Example 3 15% Bayopal | Example 4 10% Artificial Beef Flavor |
|---|---|---|---|---|---|
| Enrofloxacin | 50.0 | 50.0 | 50.0 | 50.0 | 50.0 |
| Lactose | 31.0 | 31.0 | 31.0 | 31.0 | 31.0 |
| Maize starch | 27.0 | 27.0 | 27.0 | 27.0 | 27.0 |
| PVP 25 | 3.0 | 3.0 | 3.0 | 3.0 | 3.0 |
| Microcrystalline cellulose | 8.0 | 8.0 | 8.0 | 8.0 | 8.0 |
| Bayopal | | 6.0 | 12.0 | 18.0 | |
| Artificial Beef Flavor | | | | | 12.0 |
| Colloidal silicon dioxide | 0.2 | 0.2 | 0.2 | 0.2 | 0.2 |
| Magnesium stearate | 0.8 | 0.8 | 0.8 | 0.8 | 0.8 |

Figure 1:
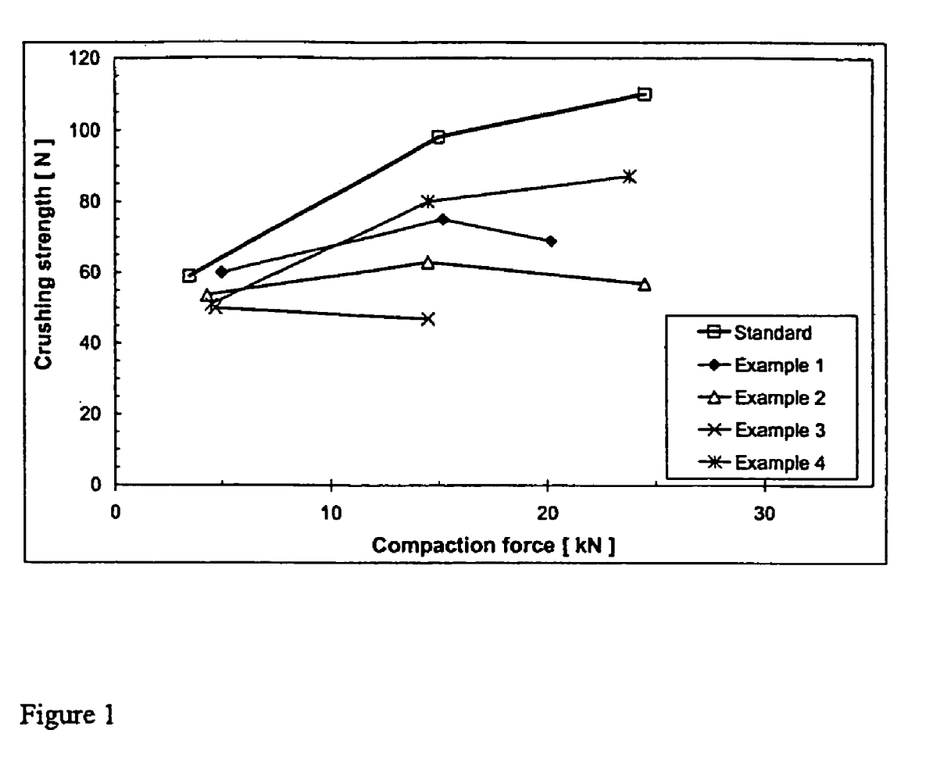
FIG. 1 shows the dependence of the resistance to crushing [N] on the load applied [kN] for Examples 1 to 4 compared with the standard.

Addition of the flavouring produces the tablet hardness as the content of the flavouring increases, as shown in FIG. 1.

Figure 2:
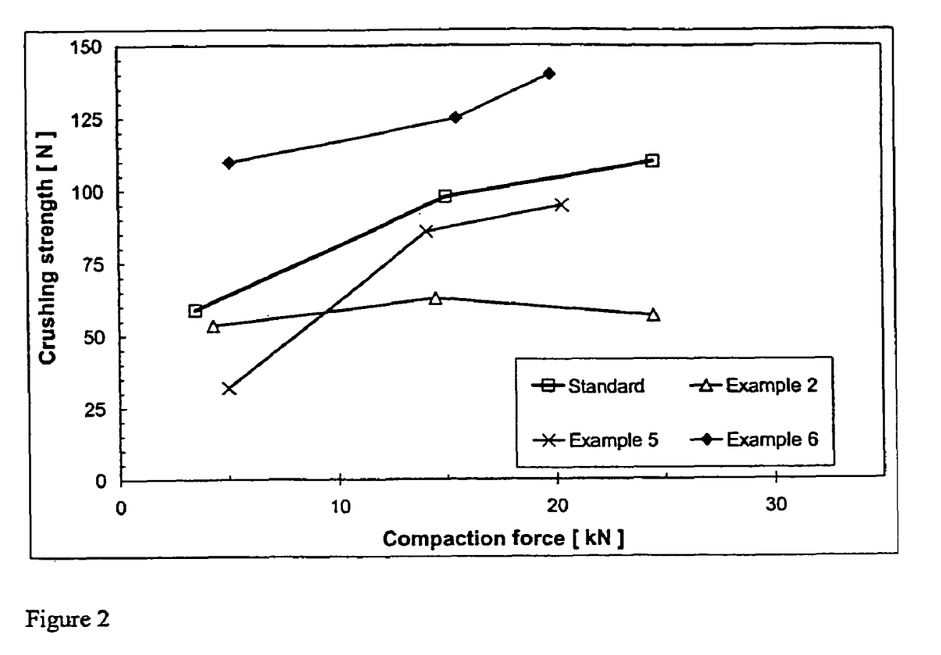
FIG. 2 shows the dependence of resistances to crushing [N] on the load applied [kN] for Examples 2, 5 and 6, and the standard.

The tablet hardness can be improved by adding large amounts of colloidal silicon dioxide (e.g. Aerosil®) and by adding further excipients (FIG. 2).

TABLE 2

| Ingredient | Standard | Example 2 10% Bayopal | Example 5 10% Bayopal + 10% Aerosil | Example 6 Additional MCC |
|---|---|---|---|---|
| Enrofloxacin | 50.0 | 50.0 | 50.0 | 50.0 |
| Lactose | 31.0 | 31.0 | 31.0 | 31.0 |
| Maize starch | 27.0 | 27.0 | 27.0 | 27.0 |
| PVP 25 | 3.0 | 3.0 | 3.0 | 3.0 |
| Microcrystalline cellulose | 8.0 | 8.0 | 8.0 | 28.0 |
| Bayopal ® | | 12.0 | 12.0 | 17.5 |
| Colloidal silicon dioxide | 0.2 | 0.2 | 12.2 | 10.0 |
| Croscarmellose sodium | | | | 7.0 |
| Magnesium stearate | 0.8 | 0.8 | 0.8 | 0.8 |

Stated amounts of ingredients in mg/tablet

II. Pradofloxacin Tablets

Various formulations were chosen for pradofloxacin (structural formula), and the influence of an added flavouring on the tablet properties was tested.

TABLE 3

Mannitol-based formulations:

|  | Example 7 | Example 8 | Example 9 | Example 10 | Example 11 |
|---|---|---|---|---|---|
| Pradofloxacin | 100 | 100 | 100 | 100 | 100 |
| Microcrystalline cellulose | 20 | 20 | 20 | 20 | 20 |
| Mannitol | 157.5 | 157.5 | 157.5 | 157.5 | 157.5 |
| PVP 25 | 15 | 15 | 15 | 15 | 15 |
| Artificial Beef Flavor |  |  |  |  | 15 |
| Bayopal ® |  | 15 | 15 | 15 |  |
| Croscarmellose sodium | 6 | 6 | 6 | 6 | 6 |
| Colloidal silicon dioxide |  |  | 15 | 3.75 | 15 |
| Magnesium stearate | 1.5 | 1.5 | 1.5 | 1.5 | 1.5 |
| Flexural strength/load ratio | $2.13 \times 10^{-3}$ | $2.00 \times 10^{-3}$ | $3.03 \times 10^{-3}$ | $2.36 \times 10^{-3}$ | $2.30 \times 10^{-3}$ |

Stated amounts of ingredients in mg/tablet
Tablet format: oblong 14 × 6 r 5 [mm]

Addition of Bayopal reduces the tablet hardness (indicated as hardness yield=flexural strength/load ratio). Compared with the flavouring-free formulation, the flexural strength of the oblong tablets decreases. The tablet hardness can be increased markedly by adding colloidal silicon dioxide, which has advantages both in manufacture (transport, packaging) and in administration of the tablets.

Figure 3:
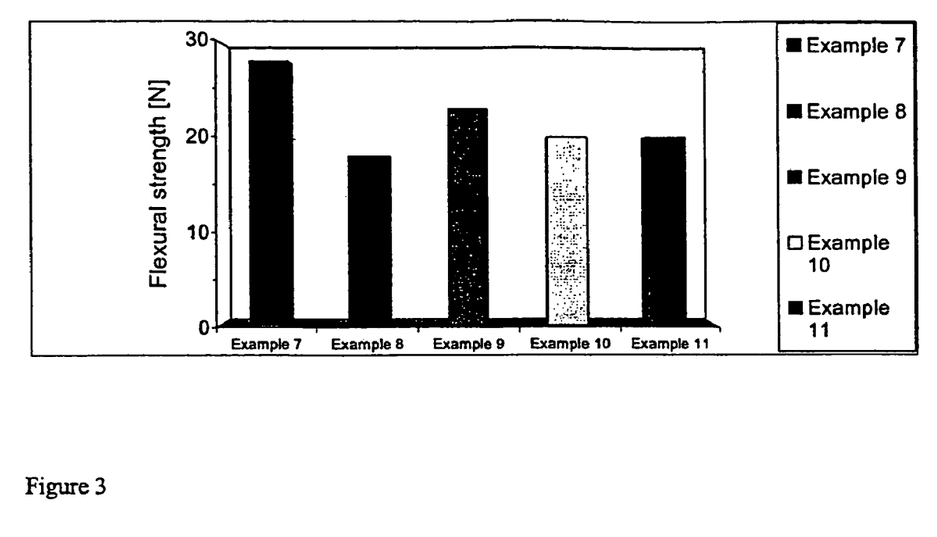
FIG. 3 shows the flexural strength [N] for Examples 7 to 11.

Additional advantages emerge for the formulations with colloidal silicon dioxide on storage under moist conditions. After storage for one week at a humidity of >80%, the flexural strength of all the tablets with flavourings is reduced. This decrease can be reduced, as shown by FIG. 3 hereinafter, to an extent acceptable for practice on use of large amounts of colloidal silicon dioxide.

The principle, which has already been described several times, of improving the tablet hardness also applies to pradofloxacin formulations based on microcrystalline cellulose. As the above table shows, addition of flavourings has particularly disadvantageous effects on the tablet hardness of these tablets, but this can be avoided by adding colloidal silicon dioxide.

Pradofloxacin tablets with lactose and microcrystalline cellulose:

The following mixture can be compressed to tablets of various sizes:

TABLE 5

| Pradofloxacin | 15.0% |
|---|---|
| Microcrystalline cellulose | 35.0% |
| Lactose | 24.0% |

TABLE 5-continued

| PVP 25 | 5.0% |
|---|---|
| Artificial Beef Flavor | 10.0% |
| Croscarmellose sodium | 7.5% |
| Colloidal silicon dioxide | 2.5% |
| Magnesium stearate | 1.0% |

Tablets with the following sizes and dosages are possible, for example:

TABLE 4

Formulations based on microcrystalline cellulose:

|  | Example 12 | Example 13 | Example 14 | Example 15 | Example 16 |
|---|---|---|---|---|---|
| Pradofloxacin | 100 | 100 | 100 | 100 | 100 |
| Microcrystalline cellulose | 152.8 | 152.8 | 152.8 | 152.8 | 152.8 |
| PVP 25 | 30 | 30 | 30 | 30 | 30 |
| Artificial Beef Flavor |  |  |  |  | 15 |
| Bayopal |  | 15 | 15 | 15 |  |
| Croscarmellose sodium | 15 | 15 | 15 | 15 | 15 |
| Colloidal silicon dioxide | 0.9 | 0.9 | 15.9 | 4.65 | 15.9 |
| Magnesium stearate | 1.35 | 1.35 | 1.35 | 1.35 | 1.35 |
| Flexural strength/load ratio | $6.53 \times 10^{-3}$ | $4.25 \times 10^{-3}$ | $5.29 \times 10^{-3}$ | $4.68 \times 10^{-3}$ | $6.46 \times 10^{-3}$ |

Stated amounts of ingredients in mg/tablet
Tablet format: oblong 14 × 6 r 5 [mm]

|  | Dosage Pradofloxacin | Tablet format |
|---|---|---|
| Example 17: | 15 mg | 8 × 4 r 4.5 [mm] |
| Example 18: | 60 mg | 14 × 7 r 6 [mm] |
| Example 19: | 120 mg | 18 × 8 r 6 [mm] |

Small tablets are particularly sensitive to moisture. On storage of the tablets from Example 17 in the open without protective packaging they retain a hardness which is sufficient for their size, as shown below and confirmed and supplemented by the findings from the preceding pradofloxacin tablet examples.

TABLE 6

Tablet hardness after storage in the open at 85% rel. humidity for 15 days:

| Load [kN] | Tablet hardness after storage in the open [N] |
|---|---|
| 9 | 32 |
| 12 | 34 |
| 13.5 | 36 |

III. Tanomastat Tablets

Tanomastat (structural formula) was investigated in the form of various taste-optimized tablets.

TABLE 7

Formulations with Artificial Beef Flavor

|  | Example 20 | Example 21 | Example 22 | Example 23 |
|---|---|---|---|---|
| Tanomastat | 200.0 | 200.0 | 200.0 | 200.0 |
| Lactose | 121.20 | 121.20 | 121.20 | 121.20 |
| Microcrystalline cellulose | 60.8 | 60.80 | 60.80 | 60.80 |
| Na lauryl sulphate | 2.0 | 2.0 | 2.0 | 2.0 |
| Artificial Beef Flavor | — | 40.0 | 40.0 | 20.0 |
| Croscarmellose sodium | 12.0 | 12.0 | 12.0 | 12.0 |
| Colloidal silicon dioxide | — | — | 10.0 | 20.0 |
| Magnesium stearate | 4.0 | 4.0 | 4.0 | 4.0 |

Stated amounts of ingredients in mg/tablet

Figure 4:
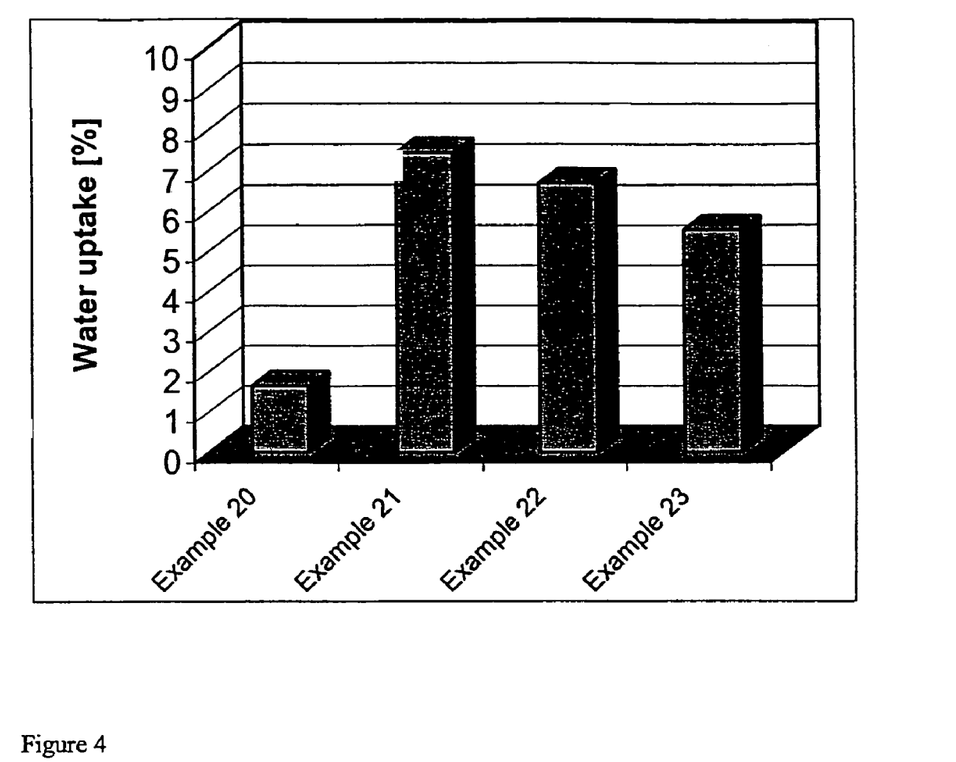
FIG. 4 shows the water uptake [%] for Examples 20 to 23 over a period of 7 days.

Example 20 is a formulation without flavouring for comparison. On storage of the flavouring-containing formulations under moist conditions, they take up water, as shown in FIG. 4 hereinafter for the exemplary formulations. This can be reduced by adding colloidal silicon dioxide in large amounts.

Figure 5:
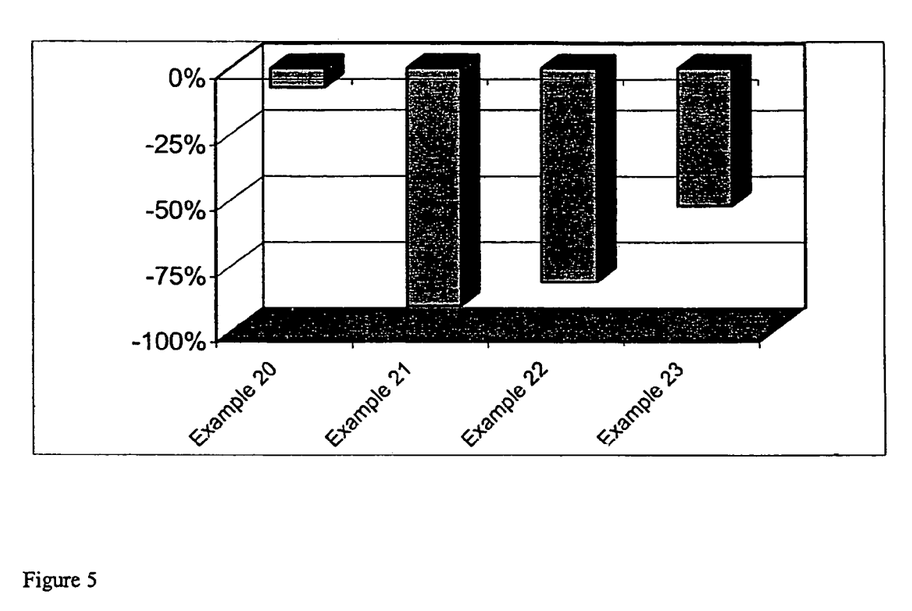
FIG. 5 shows the decrease in tablet hardness [%] for Examples 20 to 23.

During storage, the tablets additionally lose hardness to a marked extent, which may lead to problems in the market (customer complaints). This problem can also be reduced by the inventive measure (see FIG. 5).

The formulation corresponding to Example 23 can be compressed to tablets of a wide variety of sizes, as shown below by way of example:

TABLE 8

|  | Example 23 | Example 24 | Example 25 | Example 26 |
|---|---|---|---|---|
| Tanomastat | 200.0 | 50.0 | 300.0 | 400.0 |
| Lactose | 121.20 | 30.3 | 181.8 | 242.4 |
| Microcrystalline cellulose | 60.80 | 15.2 | 91.2 | 121.6 |
| Na lauryl sulphate | 2.0 | 0.5 | 3.0 | 4.0 |
| Artificial Beef Flavor | 20.0 | 5.0 | 30.0 | 40.0 |
| Croscarmellose sodium | 12.0 | 3.0 | 18.0 | 24.0 |
| Colloidal silicon dioxide | 20.0 | 5.0 | 30.0 | 40.0 |
| Magnesium stearate | 4.0 | 1.0 | 6.0 | 8.0 |
| Tablet format | 16*6 r 5 | 9*4 r 4.5 | 17*7 r 6 | 18*8 r 6 |

Stated amounts of ingredients in mg/tablet; tablet format in mm

All these formulations display the advantages described above on storage under moist conditions.

TABLE 9

Bayopal-containing formulations

|  | Example 20 | Example 27 | Example 28 | Example 29 | Example 30 |
|---|---|---|---|---|---|
| Tanomastat | 200.0 | 200.0 | 200.0 | 200.0 | 200.0 |
| Lactose | 121.20 | 121.20 | 121.20 | 121.20 | 121.20 |
| Microcrystalline cellulose | 60.80 | 60.80 | 60.80 | 60.80 | 60.80 |
| Na lauryl sulphate | 2.0 | 2.0 | 2.0 | 2.0 | 2.0 |
| Bayopal | — | 40.0 | 40.0 | 40.0 | 40.0 |
| Croscarmellose sodium | 12.0 | 12.0 | 12.0 | 12.0 | 12.0 |
| Colloidal silicon dioxide | — | — | 40.0 | 20.0 | 10.0 |
| Magnesium stearate | 4.0 | 4.0 | 4.0 | 4.0 | 4.0 |

Stated amounts of ingredients in mg/tablet

Figure 6:
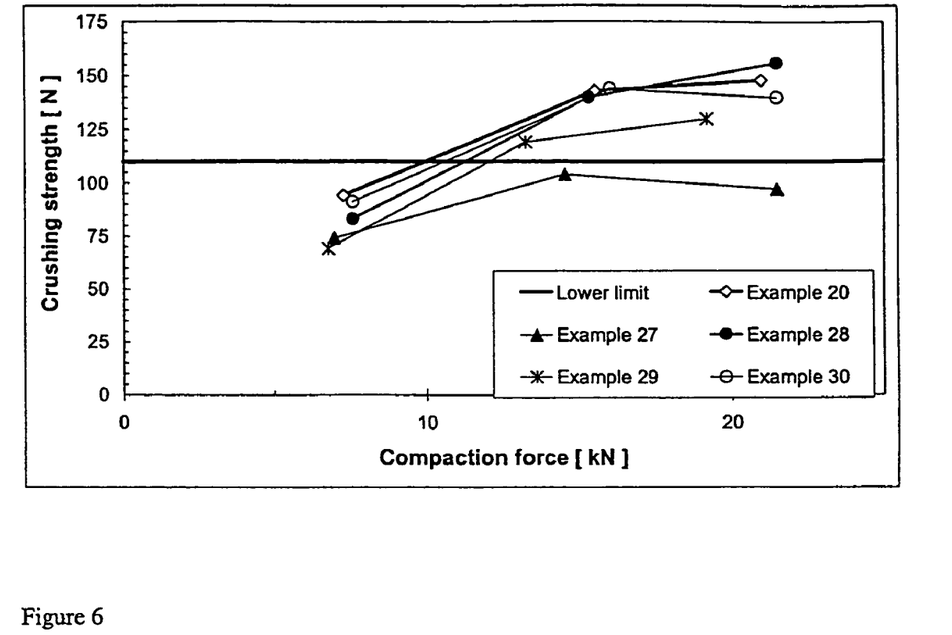
FIG. 6 shows the dependence of the resistances to crushing [N] on the load applied [kN] for Examples 20 and 27 to 30.

The formulations lose hardness through the addition of Bayopal. This can, as already described also for other active ingredients and flavourings, be avoided by adding colloidal silicon dioxide (see FIG. 6).

Besides the adverse effect on the tablet hardness, the flavouring also causes a deterioration in the disintegration and release properties. These adverse effects can also be reduced by the described inventive measure.

Figure 7:
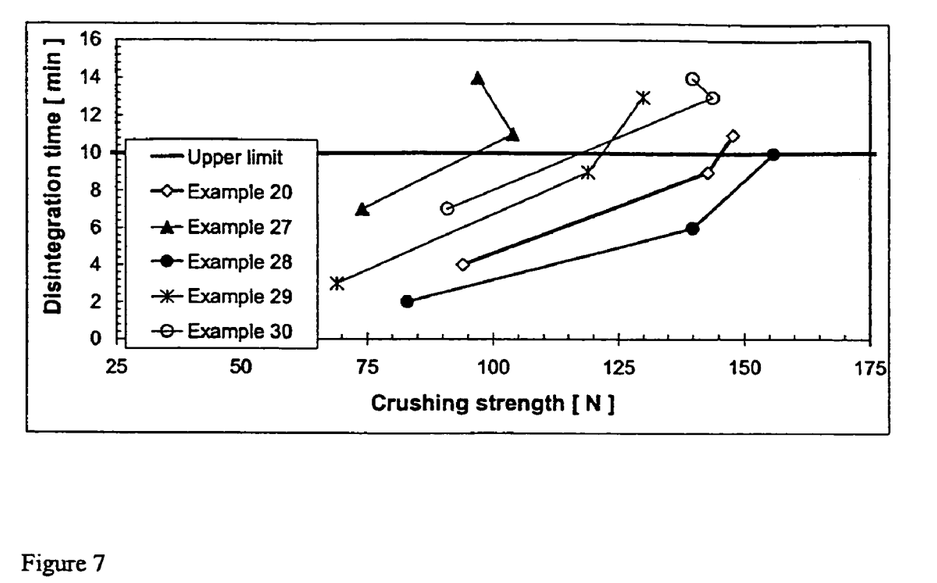
FIG. 7 shows the dependence of the disintegration time [min] on the resistance to crushing [N] for Examples 20 and 27 to 30; the upper limit for an acceptable disintegration time is indicated. The time should be far below the upper limit of 15 minutes required by the European Pharmacopoeia in order to guarantee that all the tablets always comply with the required limits. For this reason, a disintegration time of less than 10 minutes is judged to be acceptable.

Disintegration of the tablets with colloidal silicon dioxide is, despite the improved tablet hardness, faster than for tablets with flavouring without colloidal silicon dioxide (FIG. 7).

Figure 8:
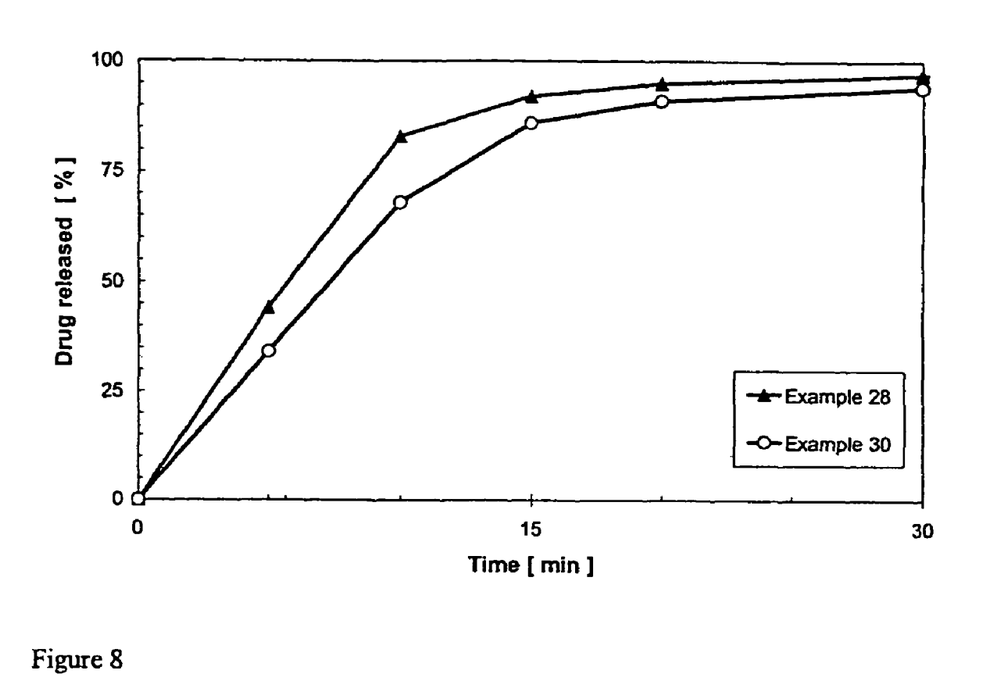
FIG. 8 shows the kinetics of release from tablets of Examples 28 and 30 after storage under moist conditions for 8 weeks. The percentage of active ingredient released is plotted against the time.

After storage under moist conditions for 8 weeks, tablets produced as tablet with 50 mg of active ingredient in analogy to the composition of Examples 28 and 30 show improved release if a large amount of colloidal silicon dioxide has been incorporated (FIG. 8).

IV. Acceptance Tests on Dogs

The formulations corresponding to Examples 23 and 24 were tested on 40 dogs. In contrast to the taste masking described in EP 00345787 or U.S. Pat. No. 4,910,023, the tested formulations were voluntarily consumed by 92.5% of the investigated dogs, proving that the added flavouring has surprisingly not lost its functionality.

V. Influence of the Production Process

Various production processes can be chosen for all the formulations described:
- addition of the flavouring and the colloidal silicon dioxide to the admixture
- aqueous granulation of the flavouring with the colloidal silicon dioxide, addition of these granules to the admixture or to the further granulation
- alcoholic (e.g. ethanolic) granulation of the flavouring with the colloidal silicon dioxide, addition of these granules to the admixture or to the further granulation
- granulation of the flavouring with the colloidal silicon dioxide using a further binder, addition of these granules to the admixture or to the further granulation
- addition of the flavouring with the colloidal silicon dioxide to the granulation of the active ingredient, possibly with addition of further excipients such as, for example, fillers, disintegrants or binders.

Figure 9:
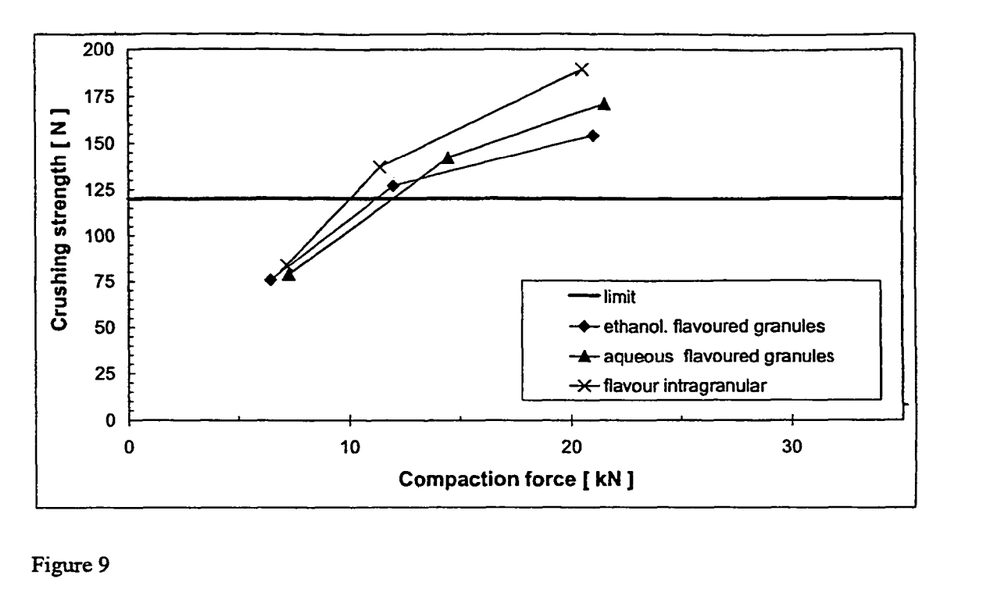
FIG. 9 shows the dependence of the resistances to crushing [N] on the load applied [kN] for tablets with the composition of Example 28 produced in various ways.

These production processes result in tablets having identical properties. This is shown in FIG. 9 for the hardness of tablets corresponding to the composition from Example 28, which were produced by different granulation processes.

Figure 10:
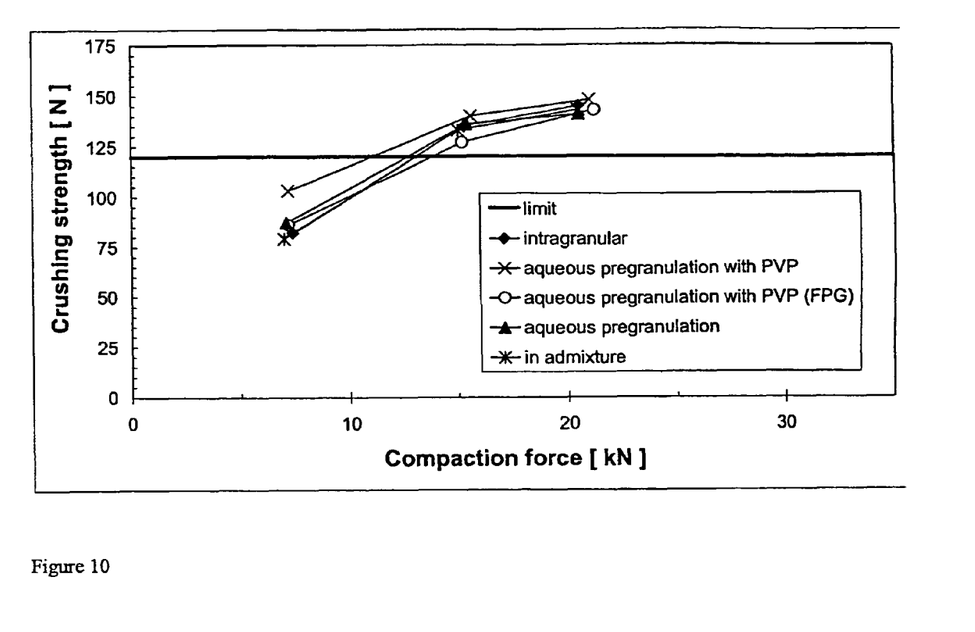
FIG. 10 shows the dependence of the resistances to crushing [N] on the load applied [kN] for tablets with the composition of Example 30 produced in various ways.

Choosing different production processes for tablets according to Example 30 likewise results in tablets having virtually identical load/hardness profiles (FIG. 10).

These data prove that the principle of incorporating large amounts of colloidal silicon dioxide in flavouring-containing formulations results in an improvement in the pharmaceutical properties of tablets, irrespective of the chosen granulation or tabletting process.

The invention claimed is:

1. A solid pharmaceutical formulation comprising:
   a. 15% by weight pradofloxacin;
   b. 35% by weight microcrystalline cellulose;
   c. 24% by weight lactose;
   d. 5% by weight polyvinylpyrrolidone;
   e. 10% by weight flavoring which is a mixture of proteins, fats, and carbohydrates, exclusing starch;
   f. 7.5% by weight croscarmellose sodium;
   g. 2.5% by weight colloidal silicon dioxide; and,
   h. 1.0% by weight magnesium stearate and wherein the formulation excludes starch.

2. A process for producing a solid pharmaceutical formulation according to claim 1, in which the flavoring is granulated with the colloidal silicon dioxide and with the pradofloxacin, the microcrystalline cellulose, lactose, polyvinylpyrrolidone, croscarmellose sodium, and magnesium stearate.

* * * * *